United States Patent
Hirao

(10) Patent No.: US 6,825,381 B2
(45) Date of Patent: Nov. 30, 2004

(54) METHOD AND APPARATUS FOR ABSORBING (METH) ACRYLIC ACID

(75) Inventor: Harunori Hirao, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/304,751

(22) Filed: Nov. 27, 2002

(65) Prior Publication Data

US 2003/0120112 A1 Jun. 26, 2003

(30) Foreign Application Priority Data

Dec. 10, 2001 (JP) ........................................ 2001-375741

(51) Int. Cl.$^7$ .............................................. C07C 51/42
(52) U.S. Cl. ................................................... 562/600
(58) Field of Search ............................... 562/600, 542, 562/532

(56) References Cited

U.S. PATENT DOCUMENTS

| 5,780,679 A | * | 7/1998 | Egly et al. ................... 562/600 |
| 5,785,821 A | | 7/1998 | Sakamoto et al. |
| 6,051,736 A | * | 4/2000 | Schraut et al. ............... 562/600 |
| 6,407,287 B2 | * | 6/2002 | Matsunobo et al. ......... 562/532 |
| 6,566,551 B2 | * | 5/2003 | Nishimura et al. .......... 562/542 |

FOREIGN PATENT DOCUMENTS

JP 9-157213 6/1997

* cited by examiner

*Primary Examiner*—Rita Desai
*Assistant Examiner*—Hector M. Reyes
(74) *Attorney, Agent, or Firm*—Wenderoth, Lind & Ponack, L.L.P.

(57) ABSTRACT

The object of the present invention is to provide a method to suppress changes the concentration of (meth)acrylic acid in the bottom solution discharged from the absorption column, and to enable stable operation for separating and purifying (meth)acrylic acid in the subsequent steps onward.

The above-mentioned object can be achieved by way of changing the water amount contained in the gas exhausted from the top portion of the absorption column.

14 Claims, 1 Drawing Sheet

METHOD AND APPARATUS FOR ABSORBING (METH) ACRYLIC ACID

BACKGROUND OF THE INVENTION

1. Field of the Invention

The present invention relates to a method and an apparatus for absorbing (meth)acrylic acid, and more particularly to a method and an apparatus for absorbing (meth)acrylic acid, in both of those which the concentration of (meth) acrylic acid in an absorption column bottom solution discharged from the absorption column is controlled by means of changing the water amount contained in a gas which is exhausted from the absorption column.

2. Description of the Prior Art

Easily-polymerizable compounds, such as acrylic acid and methacrylic acid, are used as a raw material for producing industrial products and are produced in a large scale in a big plant. In general, these compounds are manufactured via various absorbing and purifying processes in order to obtain them in a highly-purified state.

For example, in the process of manufacturing acrylic acid, when propylene, propane, acrolein and the like are subjected to a catalytic gas-phase oxidation with gas containing oxygen in the molecular state in the presence of an oxidizing catalyst, substances with low boiling points such as acetic acid, lower aldehydes or water and substances with high boiling point such as furfural or maleic anhydride are generated as the by-products in addition to acrylic acid as the target compound. Consequently, the mixed gas obtained is led into an absorption column for absorbing acrylic acid (hereinafter referred to as "absorption column"), where the mixed gas is contacted with absorbent to thereby absorb and collect acrylic acid into the absorbent. Thus, a solution containing acrylic acid and the other by-products is obtained. Then, acrylic acid is separated and purified from the solution by employing distillation, stripping, extraction, crystallization techniques or the like so that acrylic acid is obtained as a commercial product.

Such a separation and purifying process is disclosed in the U.S. Pat. No. 5,785,821, where a mixed gas obtained by oxidizing propylene or the like by way of catalytic gas-phase oxidation is led into the acrylic acid absorption column, contacted with the absorbent to thereby obtain the acrylic acid aqueous solution of the mixed gas (also referred to as a "bottom solution"), and the obtained acrylic acid aqueous solution is led into an azeotropic distillation column wherein acrylic acid is obtained.

Since water is inexpensive, has high capability for absorbing (meth)acrylic acid and acrylic acid solution having relatively high concentration can be obtained, an absorbent containing water as the main component is generally used in the foresaid absorbing process for absorbing (meth) acrylic acid from a gas containing (meth)acrylic acid. Further, in the foresaid absorbing process, since almost no particular attention has been paid with regard to the pressure and temperature in the top portion of the absorption column in the past, there is substantially no change in the water amount contained in the gas exhausted from the top portion of the absorption column.

In general, in the process of the catalytic gas-phase oxidation, the air is used as the gas containing oxygen in the molecular state because it is inexpensive. However, when the air is used, due to changes in the atmospheric conditions or the like, variation in the water amount contained in the air to be delivered into the reactor is inevitable. Accordingly, the water content in the gas containing acrylic acid to be introduced into the absorption column fluctuates as well. As a result, the concentration of (meth)acrylic acid in the bottom solution, which is discharged from the bottom of the absorption column, varies. This variation in the concentration of (meth)acrylic acid affects the stabilized operation for separating and purifying (meth)acrylic acid in the subsequent steps onward or cause variation in the amount of waste water.

As a countermeasure for the above problem, it has been proposed to adjust the water concentration of the air to be used in the catalytic gas-phase oxidation process at a constant concentration level. However, the implementation of such countermeasure is not satisfactory and feasible since expenditures for installing such moisture adjusting facility and utilities are too much burden.

As the alternative countermeasure in order to stabilize the (meth)acrylic acid concentration of bottom solution, there is an idea to control the supply amount of the absorbent introduced into the absorption column corresponding to the water amount fed into a reactor that performs the catalytic gas-phase oxidation process. However, when the waste water is recovered and recycled to be used as the absorbent, if it is intended to maintain the volumetric ratio of the waste water with respect to the supply amount of the absorbent (hereinafter referred to as "recovery ratio of the absorbent") to be a constant ratio, it is inevitable to change the amount of the waste water to be recovered and recycled in response to the change in the supply amount of the absorbent. As a result, it becomes inevitable to change the amount of the waste water to be thrown out.

Even though an adjustment of said changes in the waste water amount by way of changing the recovery ratio is attempted, on the other hand, it is required to generally set the recovery ratio at a low ratio since the upper limit of the recovery ratio is fixed to 100%, whereby the amount of the waste water to be finally thrown out increases.

Therefore, as described above, the countermeasures having been implemented in the past for securing the stabilized operation of the process including the waste water processing facility against the effect of the changes in the atmospheric conditions and the like was not satisfactory.

SUMMARY OF THE INVENTION

The inventor of the present invention had examined in detail about the supply amount of the absorbent, the amount of the waste water, the concentration of (meth)acrylic acid in the bottom solution and the changes in the absorbing coefficient in order to find a countermeasure for securing the stabilized operation including the waste water processing facility in the subsequent steps against the changes in the atmospheric conditions and the like. As a result, it was found out that all of the problems can be settled by adjusting the water amount in the gas exhausted from the top portion of the absorption column.

Specifically, although the amounts of (meth)acrylic acid and the other by-products fed out of the reactor are substantially constant since the conditions for the catalytic gas-phase oxidation reaction is constant, only the water content changes according to the changes in the atmospheric conditions and the like. Consequently, when the supply amount of the absorbent is fixed at a constant one, maintaining of the concentration of (meth)acrylic acid in the bottom solution causes to maintain the flow rate of the bottom solution, whereby resulting in stabilization in the amount of the waste water. Moreover, surprisingly, the absorbing method according to the present invention leads to less variation in the absorbing coefficient comparing to the method of changing the supply amount of the absorbent.

Accordingly, with the method according to the present invention, it is possible to secure stabilized operation in the subsequent steps including the waste water processing facility while suppressing the variation in the loss of (meth) acrylic acid from the absorption column and from the waste water to the minimum level.

The absorbing method for (meth)acrylic acid according to the present invention that can exert the above-described operations and effects is that, in a manufacturing process for (meth)acrylic acid including steps adapted to manufacture a gas containing (meth) acrylic acid by employing a catalytic gas-phase oxidation reaction and to subsequently introduce the gas into the absorption column for absorbing a target product in a form of the solution by using an absorbent containing water as the main component, characterized in that the concentration of (meth)acrylic acid in a bottom solution discharged from an absorption column is controlled by changing the water amount contained in the gas which is exhausted from the top portion of the absorption column.

In the above-described process, it is preferable to change the water amount contained in the gas exhausted from the top portion of the absorption column by the temperature and pressure in the top portion of the absorption column and to recycle a part or the whole of the waste water drained during the (meth)acrylic acid manufacturing process for use as the absorbent.

In addition, such operation to change the water amount contained in the gas exhausted from the top portion of the absorption column is preferably carried out corresponding to the water amount contained in the gas which is introduced into the reactor for the catalytic gas-phase oxidation in said catalytic gas-phase oxidation reaction or the water content contained in the air.

Further, the apparatus for absorbing (meth)acrylic acid according to the present invention is characterized in being an absorption column for carrying out the above-described process and including means for controlling the temperature in the top portion of the absorption column and/or means for controlling the pressure in the top portion of the same.

DETAILED DESCRIPTION OF THE PREFERRED EMBODIMENTS OF THE INVENTION

Figure 1:
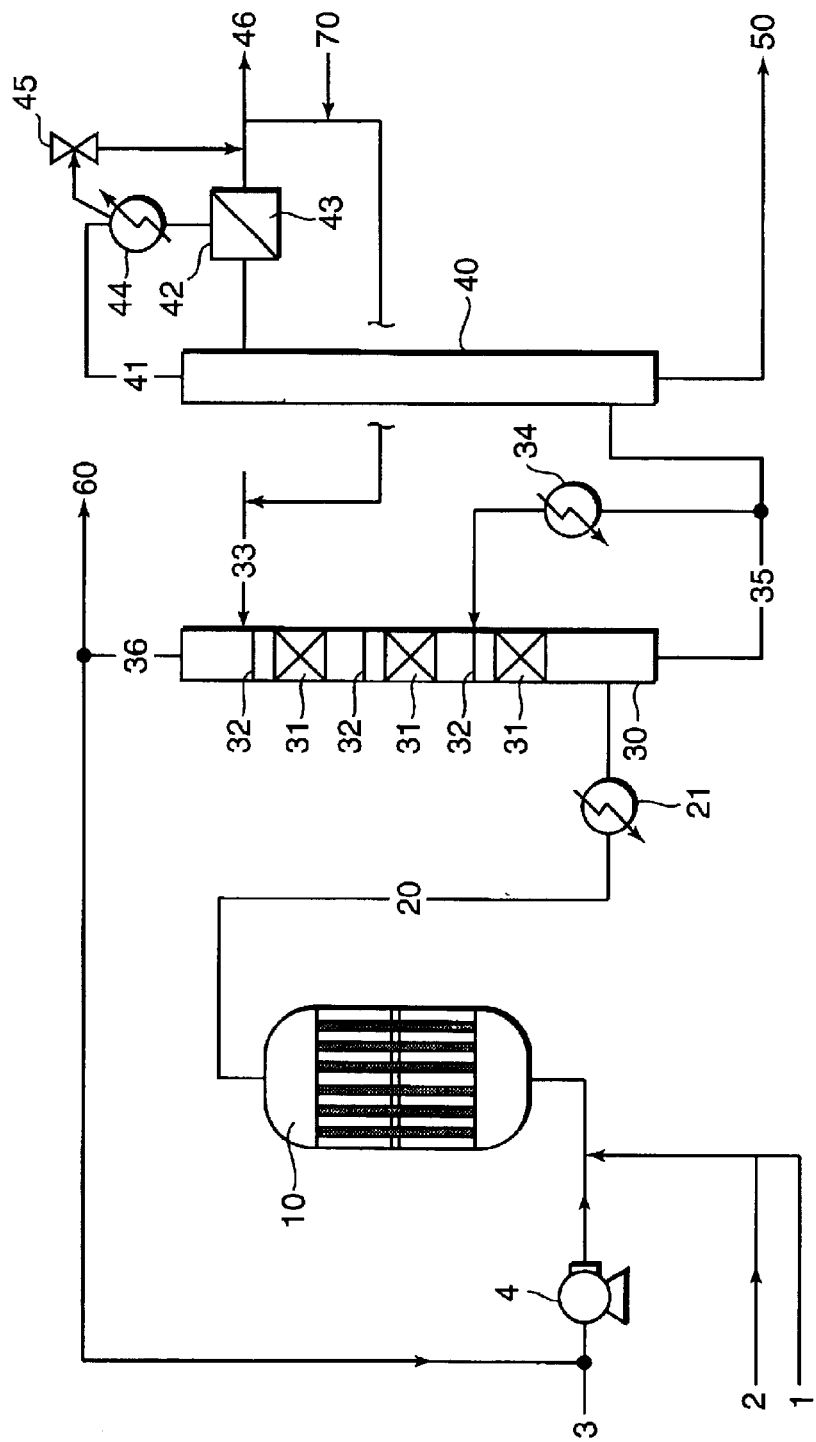
FIG. 1 is a schematic diagram showing an example of the process for manufacturing (meth)acrylic acid.

The present invention will now be specifically explained below by taking a method for manufacturing acrylic acid as the representative example with reference to FIG. 1.

First, a raw material reaction gas 1 consisting of a raw material component, such as propylene, propane and acrolein, is supplied into a catalytic gas-phase oxidation reactor 10, in which an oxidation catalyst has been charged, together with an inert gas 2 or the like and a gas 3 containing oxygen in the molecular state, such as air of which pressure having been raised by means of a blower 4. Then, a catalytic gas-phase oxidation reaction is taken place to thereby produce a gas 20 containing acrylic acid. Any type of the catalytic gas-phase oxidation reaction may be used without limitation as far as acrylic acid can be produced in the presence of a catalytic gas-phase oxidation catalyst. However, the reaction employing a multi-tubular reactor is preferably used since it gives excellent reaction efficiency. More specifically, a predetermined amount of the raw material reaction gas consisting of a raw material component 1, such as propylene, propane or acrolein, an inert gas 2, and gas 3 containing oxygen in the molecular state is supplied into a reactor such as a multi-tubular reactor, in which oxidation catalyst has been charged. Then, the raw material reaction gas is allowed to the catalytic gas-phase oxidation reaction. At this stage, if propylene is used as the raw material component, acrolein is produced at first. Then, when the acrolein is further allowed to the catalytic gas-phase oxidation, acrylic acid is produced. The reaction process that is employed in the present invention may be one step process, where the above reactions are carried out in a single reactor, or two-step process, where the above reactions are carried out separately in different reactors. Any conditions having been applied to the conventional reaction process for producing acrylic acid can be applied to the reaction of the present invention including the type of the oxidation catalyst, the raw material components, the gas concentration of such as oxygen in the molecular state or inactive gas, temperature for the reaction and so on.

As the raw material component, for example, any of propylene, propane and acrolein, or a mixture of two or more thereof can be used. The content of the raw material component is preferably in a range of 6 to 20% by volume, and preferably 8 to 15% by volume on the basis of the raw material reaction gas to be supplied to the reactor. The raw material reaction gas contains oxygen being in the molecular state in an amount 1 to 3 times (molar ratio) the raw material component in order to effect the oxidation reaction, and the rest contained therein is consisted of inactive gases, such as nitrogen, carbon dioxide, and steam.

For manufacturing acrylic acid by causing the catalytic gas-phase oxidation reaction of propylene, an oxidation catalyst generally used for the manufacturing of acrolein from the raw material gas containing propylene by catalytic gas-phase oxidation may be used as the catalyst for the former-stage reaction for the production of acrolein by employing the catalytic gas-phase oxidation of propylene. Similarly, there is no specific limitation for the catalyst which is used for the latter-stage reaction producing acrylic acid by means of the catalytic gas-phase oxidation of acrolein obtained in the foresaid former-stage reaction, and any oxidation catalyst being generally used in the manufacturing of acrylic acid by means of the catalytic gas-phase oxidation of the reaction gas containing acrolein can be used for the manufacturing of acrylic acid.

Generally, the gas containing acrylic acid that is obtainable by the catalyst gas-phase oxidation reaction has reached at a temperature ranging from 200 to 350° C. Therefore, the foresaid gas is required to be cooled down by means of a heat exchanger 21 to preferably a temperature range of from 100 to 300° C., and particularly preferably to a temperature range of from 130 to 270° C. before the gas is supplied to the absorption column adapted to absorb acrylic acid. As such a heat exchanger 21 to be used in the foresaid cooling operation, a publicly-known heat exchanger can be used. In this cooling, it is important to secure such that the temperature of the gas mixture produced by the reaction should not drop to a temperature level lower than its dew point. Note that the cooling operation is not necessary if the temperature of the gas mixture produced by the reaction is already in the above-described appropriate range.

In the acrylic acid-containing gas obtained by the catalytic gas-phase oxidation reaction, acrylic acid, oxygen being in the molecular state, the raw material components having been not yet reacted and inactive gases are contained. In addition to the foresaid gases, impurities, such as water, acetic acid, propionic acid, maleic acid, acetone, acrolein, furfural and formaldehyde produced as the by-product, are contained in said acrylic acid-containing gas.

Next, the obtained acrylic acid-containing gas 20 is introduced into the absorption column 30 in which packing (tray) 31 and distributor 32 are installed to contact the gas with the absorbent 33 to thereby prepare the bottom solution dischrged from the absorption column into the acrylic acid-containing solution ("bottom solution") 35. The part of the acrylic acid-containing solution is circulated in the acrylic acid absorption column 30 while cooling said solution by means of a cooler 34, and the rest of said solution is taken out of the absorption column and then introduced into a water separation column 40 for dehydration processing therein. Although there is no particular limitation for the absorbent used in the above stage as far as it contains water as the main component, it is preferable to recycle a part or the whole of waste water drained during the manufacturing process of acrylic acid and waste water from the vacuum equipment described later for this purpose from the economical viewpoint. Furthermore, waste water for cleaning can be incorporated into the above-mentioned waste water, if appropriate.

Besides, as the method to contact the acrylic acid-containing gas with the absorbent, a publicly-known contacting method may be employed. Examples of the contacting method include the cross flow contact using any of bubble cap trays, uniflux trays, sieve trays, jet trays, valve trays, venturi trays and optional combinations thereof, and the counterflow contact using any of turbo grid trays, dual flow trays, ripple trays, kittel trays, random packings, structured packings, and optional combinations thereof. In particular, the contacting method to contact the acrylic acid-containing gas with the absorbent by way of the counterflow contact is advantageous. In this method, it is further advantageous to set packings and/or trays having higher absorption efficiency at the upstream side of the absorbent flowing in the absorption column and to set packings and/or trays having relatively lower polymerizability at the downstream side of the absorbent flowing in the absorption column.

Although there is no particular limitation for the dehydration process in the water separation column 40, it is general to employ azeotropic distillation method in which a hardly-water-soluble azeotropic solvent is used. In this method, acrylic acid as the target product is obtained mainly as the tower bottom liquid of the water separation column 40. In this method, however, the obtained acrylic acid is transferred to the subsequent step 50 for further purifying since there is a possibility that said acrylic acid yet contains impurities such as substances having low boiling points and high boiling points. On the other hand, the impurity in the acrylic acid-containing solution (the absorption column bottom solution) 35 is distilled together with said hardly-water-soluble azeotropic solvent as a distillate gas 41 so that the impurities are separated from the acrylic acid. The distillate gas 41 is condensed by a condenser 44 being installed in the top portion of the water separation column 40 and the condensed solution is then phase-separated into an oil layer 42 and a water layer 43.

The phase-separated oil layer 42 is fed back to the water separation column 40 and used for the recycle, and the water layer 43 is treated as waste water 46 together with the waste water from the vacuum equipment 45. However, since there is a possibility that slight amount of acrylic acid is yet contained in the water layer, it is preferable in economical point of view and for decreasing the amount of the waste water to collect a part or the whole of the water layer so as to use it for the absorbent 33. Also, apart or the whole of the waste water drained from the subsequent step 50 and the waste solution (recovered water 70) from the vacuum equipment can be used for the absorbent 33. Further, waste water for cleaning the apparatuses can be incorporated into the above-described waste water so as to use it for the absorbent 33, if appropriate.

The entire gas 36 exhausted from the top portion of the absorption column 30 may be treated as waste gas 60. However, it is advantageous for decreasing the supply amount of said inert gas 2 or the like to circulate a part of said gas 36 as a recycle gas to the reactor 10 by means of, for example, the blower 4.

In the present invention, the water amount in the gas exhausted from the top portion of the absorption column is changed in the absorbing step to thereby control the concentration of (meth)acrylic acid contained in the bottom solution 35 discharged from the absorption column 30 while maintaining the supply amount of the absorbent 33 at a constant level. In the above control operation, there is no particular limitation for the method to change the water amount contained in the gas exhausted from the top portion of the absorption column, and it is preferable to employ a method, for example, that changes either one or both of the temperature and the pressure in the top portion of the absorption column.

For example, when the water content in the air to be used as said gas containing oxygen in the molecular state is greater in the step of the catalytic gas-phase oxidation, that is when the water concentration in the air is greater, the concentration of (meth)acrylic acid in the bottom solution discharged from the absorption column can be stably maintained by any way of elevating the temperature in the top portion of the absorption column, descending the pressure in said top portion, or carrying out the both operations. Contrary thereto, when the water amount contained in the air is less, the concentration of (meth)acrylic acid may be maintained by performing the inverse operations to the above-mentioned operations.

As a method to change the temperature in the top portion of the absorption column 30, it is possible to employ any of a method to change the heat-eliminating capability of the cooler 34, a method to newly install another cooler in a location other than that of the cooler 34 and to change the heat-eliminating capability of the newly-installed cooler, a method to change the temperature of the absorbent 33, and a method to change the temperature of the gas 20 containing acrylic acid. Said methods may be employed either solely or in a combined manner. In addition, as the method to change the pressure in the top portion of the absorption column 30, a conventional method, for example, that uses pressure controlling valves may be employed.

The cycle to change the water amount in the gas exhausted from the top portion of the absorption column may be set in considering the allowable changes in the subsequent steps including the waste water processing facility and the change in the atmospheric conditions and the like. Therefore, there is no particular limitation for the cycle, and it is not required to set the cycle, for example, for every second, every minute, every hour, every day, every month, and every season.

Although there is no limitation for the concentration of acrylic acid in the solution that is taken out of the bottom of the absorption column, it is preferable that the concentration is in a range of from 60 to 85% by weight. Because, if the concentration is lower than 60% by weight, not only the construction cost for the subsequent steps and utility fees, both of those which are required for the separation of the impurities, but also the amount of the waste water increase. On the other hand, if the concentration is set to be higher than 85% by weight, the loss of acrylic acid from the top portion of the absorption column increases. In that case, in order to decrease the loss, it is required to increase the number of theoretical plate in the absorption column, which, however, further increases the cost for the plant construction.

Besides, though there is no particular limitation for the temperature in the top portion of the absorption column, it is preferable for the temperature to be in a range of from 40 to 80° C. Because, if the temperature is lower than 40° C., not only the construction cost and utility fees for the cooling are required but also the concentration of acrylic acid in the solution taken out of the bottom of the absorption column is lowered due to increase of condensed substances having lower boiling points than that of acrylic acid and the amount of the waste water increase. Besides, if the temperature is higher than 80° C., the loss of acrylic acid from the top portion of the absorption column increases to thereby unfavorably raise the production cost of acrylic acid.

Also, though there is no particular limitation with respect to the foresaid pressure in the top portion of the absorption column, it is preferable for the pressure to be in a range of from 0 to 30 kPa (gauge pressure). Because, if the pressure is lower than 0 kPa (gauge pressure), the absorbing apparatus requires to include a vacuum device, which increases the cost for constructing the apparatus and utilities. On the other hand, if the pressure is higher than 30 kPa (gauge pressure), it is not economical in terms of increasing the construction cost and more utility charge because a larger-sized blower for supplying the raw material gas to the reactor performing the catalytic gas-phase oxidation reaction is required.

Now, the present invention will be explained further in detail with reference to the following examples. However, it should be noted that the present invention is not limited to the description in the examples.

Note that the absorbing coefficient of acrylic acid in the absorption column and the recovery ratio of the absorbent (the ratio of waste water contained in the supply amount of the absorbent) are respectively calculated in accordance with the following equations.

Absorbing Coefficient of Acrylic Acid=1−(Amount of Acrylic Acid in Gas exhausted from Top Portion of Absorption Column/Amount of Acrylic Acid in Gas at Inlet of Absorption Column)

Recovery Ratio of Absorbent=Recovered Amount of Waste Water/Supply Amount of Whole Absorbents

REFERENCE EXAMPLE

Into a multi-tubular reactor for the catalytic gas-phase oxidation reaction in which a catalyst has been charged, was introduced a reaction gas with a composition consisting of 8.0% by volume of propylene, 14.4% by volume of oxygen, 5.2% by volume of water, 71.7% by volume of nitrogen and 0.7% by volume of others (propane, $CO_x$, acrylic acid, acetic acid, aldehydes, etc.) at a flowing rate of 34,780 $Nm^3$ per hour so that the catalytic gas-phase oxidation reaction is performed. As a result of the reaction, acrylic acid-containing gas with a composition consisting of 7.1% by volume of acrylic acid, 14.5% by volume of water, 73.5% by volume of nitrogen, 1.4% by volume of oxygen and 3.5% by volume of others (propylene, propane, $CO_x$, acetic acid, aldehydes, etc.) was obtained.

The obtained gas was then supplied into the absorption column, and the absorbing of acrylic acid was performed in the absorption column under a condition of using the absorbent containing 92.8% by weight of water (flow rate: 4.54 $m^3$/hour), setting a pressure in the top portion of the absorption column at 10.8 kPa (gauge pressure), setting a temperature in the top portion at 62.8° C., and setting there recovery ratio of the absorbent to 0.8.

After the above absorbing operation, it was noted that the concentration of acrylic acid in the solution taken out of the bottom of the absorption column was 70.0% by weight, the absorbing coefficient of acrylic acid was 0.987, and the amount of waste water drained during the acrylic acid production process was 1.60 $m^3$/hour.

Example 1

The catalytic gas-phase oxidation reaction was performed in the same procedures as those described in the above Reference Example except that the contents of water and nitrogen in the reaction raw material gas were set to 7.4% by volume and 69.5% by volume, respectively to thereby obtain the acrylic acid-containing gas with a composition consisting of 7.1% by volume of acrylic acid, 16.6% by volume of water, 71.3% by volume of nitrogen, 1.4% by volume of oxygen and 3.6% by volume of others (propylene, propane, $CO_x$, acetic acid, aldehydes, etc.).

The obtained gas was then supplied into the acrylic acid absorption column, and the water amount contained in the gas exhausted from the top portion of the absorption column was changed by means of adjusting the temperature in the top portion of the absorption column so that the pressure in the top portion of the absorption column, the supply flow rate of the absorbent, the concentration of acrylic acid in the solution taken out of the bottom of the absorption column and the recovery ratio of the absorbent were set to 10.8kPa (gauge pressure), 4.54$m^3$/hour, 70.0% by weight and 0.8, respectively, which are the same condition as those in the above-described Reference Example. Under such a condition, absorbing operation of acrylic acid was performed, and as a result, a satisfactory absorbing condition was obtained when the temperature in the top portion of the absorption column was 65.1° C.

In the above satisfactory condition, the water content in the absorbent, the absorbing coefficient of acrylic acid and the amount of the waste water drained during the acrylic acid manufacturing process were 93.2% by weight, 0.982 and 159$m^3$/hour, respectively.

Example 2

The catalytic gas-phase oxidation reaction was performed in the same procedures as those described in the above Reference Example except that the contents of water and nitrogen in the reaction raw material gas were set to 6.8% by volume and 70.1% by volume, respectively to thereby obtain the acrylic acid-containing gas with a composition consisting of 7.1% by volume of acrylic acid, 16.1% by volume of water, 71.9% by volume of nitrogen, 1.4% by volume of oxygen and 3.5% by volume of others (propylene, propane, $CO_x$, acetic acid, aldehydes, etc.).

The obtained gas was then supplied into the acrylic acid absorption column, and the water amount contained in the gas exhausted from the top portion of the absorption column was changed by means of adjusting the temperature in the top portion of the absorption column so that the pressure in the top portion of the absorption column, the supply flow rate of the absorbent, the concentration of acrylic acid in the bottom solution to be taken out of the bottom of the absorption column and the recovery ratio of the absorbent were set to 10.8 kPa (gauge pressure), 4.54 m³/hour, 70.0% by weight and 0.8, respectively, which are the same condition as those in the above-described Reference Example. Under such a condition, absorbing operation of acrylic acid was performed, and as a result, a satisfactory absorbing condition was obtained when the temperature in the top portion of the absorption column was 64.5° C.

In the above satisfactory condition, the water concentration in the absorbent, the absorbing coefficient of acrylic acid and the amount of the waste water drained during the acrylic acid manufacturing process were 93.1% by weight, 0.984 and 1.59 m³/hour, respectively.

Example 3

In Example 2, a absorbing operation to absorb acrylic acid was carried out in a manner of changing the water amount contained in the gas that is exhausted from the top portion of the absorption column by means of adjusting the pressure in the top portion of the absorption column so that the conditions for the acrylic acid absorption column such as a temperature in the top portion of the absorption column, the supply flow rate of the absorbent, the concentration of acrylic acid in the bottom solution to be taken out of the bottom of the absorption column and the recovery ratio of the absorbent were set to 62.8° C., 4.54 m³/hour, 70.0% by weight and 0.8, respectively, which are the same conditions as those in the above-described Reference Example. As a result, a satisfactory absorbing condition was obtained when the pressure in the top portion of the absorption column was 2.5 kPa (gauge pressure).

In the above satisfactory condition, the water concentration in the absorbent, the absorbing coefficient of acrylic acid and the amount of the waste water drained during the acrylic acid manufacturing process were 93.1% by weight, 0.984 and 1.59 m³/hour, respectively.

Comparative Example 1

In Example 2, a absorbing operation to absorb acrylic acid was carried out by setting conditions for the acrylic acid absorption column such as a pressure in the top portion of the absorption column, a temperature in said top portion, a supply flow rate of the absorbent, and there recovery ratio of the absorbent were set to 10.8 kPa (gauge pressure), 62.8° C., 4.54 m³/hour and 0.8, respectively, which are the same conditions as those in the above-described Reference Example. As a result, the concentration of acrylic acid in the bottom solution to be taken out of the bottom of the absorption column was lowered to 66.5% by weight, whereby a need has arisen to change the operational conditions in the subsequent step onward.

In the above operation, it was noted that the water content in the absorbent was 93.5% by weight, the absorbing coefficient was 0.988, and the amount of the waste water drained during the acrylic acid manufacturing process was 2.19 m³/hour.

Comparative Example 2

In Example 2, a absorbing operation to absorb acrylic acid was performed under the same conditions in respect of the acrylic acid absorption column as those in the Comparative Example 1, that is, at a pressure in the top portion of the absorption column of 10.8 kPa (gauge pressure), at a temperature in the top portion of 62.8° C., and with setting a recovery ratio of the absorbent to 0.8, and after fixing the concentration of acrylic acid in the solution taken out of the bottom of the absorption column to 70.0% by weight by means of adjusting the amount of the absorbent. As a result, a satisfactory condition was obtained when the amount of the absorbent was set to 3.95 m³/hour.

In the above absorbing operation, it was noted that the concentration of water in the absorbent was 93.3% by weight, the absorbing coefficient was 0.982, and the amount of the waste water drained during the acrylic acid manufacturing process was 2.06 m³/hour.

Briefing

The results of the above-described Examples are summarized in Table 1.

TABLE 1

| | Content of Water in the Raw Material Gas | Pressure in the top portion | Temperature in the top portion | Supply flow rate of the Absorbent | Concentration of Acrylic Acid | Absorbing Coefficient of Acrylic Acid | Amount of the Waste Water |
|---|---|---|---|---|---|---|---|
| Reference Example | 5.2% (by volume) | 10.8 kPa | 62.8° C. | 4.54 m³/h | 70.0% (by weight) | 0.987 | 1.60 m³/h |
| Example 1 | 7.4% (by volume) | 10.8 kPa | 65.1° C. | 4.54 m³/h | 70.0% (by weight) | 0.982 | 1.59 m³/h |
| Example 2 | 6.8% (by volume) | 10.8 kPa | 64.5° C. | 4.54 m³/h | 70.0% (by weight) | 0.984 | 1.59 m³/h |
| Example 3 | 6.8% (by volume) | 2.5 kPa | 62.8° C. | 4.54 m³/h | 70.0% (by weight) | 0.984 | 1.59 m³/h |
| Comparative Example 1 | 6.8% (by volume) | 10.8 kPa | 62.8° C. | 4.54 m³/h | 66.5% (by weight) | 0.988 | 2.19 m³/h |
| Comparative Example 2 | 6.8% (by volume) | 10.8 kPa | 62.8° C. | 3.95 m³/h | 70.0% (by weight) | 0.982 | 2.06 m³/h |

As it can be seen from the results of Example 1, even when the water concentration in the reaction raw material gas to be used in the catalytic gas-phase oxidation reaction is 7.4% by volume that is higher than that in the above-described Reference Example (5.2% by volume), it was successfully achieved to maintain the concentration of acrylic acid in the bottom solution discharged from the bottom of the absorption column and the amount of waste water drained during the manufacturing process at a constant level, respectively, by controlling the temperature in the top portion of the absorption column without requiring to change the amount of the absorbent to be supplied to the absorption column and lowering the absorbing coefficient for acrylic acid.

It was noted that the same results as those of Example 1 are obtainable in Example 2, where the water concentration in the reaction raw material gas is set to 6.8% by volume.

Also, Example 3 showed that the manufacturing of acrylic acid can be successfully completed over the whole process, where the same conditions as those in Example 2 are applied and the control was attempted by adjusting the pressure in the top portion of the absorption column instead of the temperature in said top portion.

Dissimilarly, in the Comparative Example 1 where the same conditions as those in the Reference Example are applied, and the temperature and pressure in the top portion of the absorption column are maintained at constant levels in spite of high water content of 6.8% by volume in the reaction raw material gas, though the absorbing coefficient for acrylic acid can be maintained if the same supply amount of the absorbent as that in the Reference Example or the Examples is applied, the concentration of acrylic acid in the bottom solution is lowered and the amount of the waste water increases. Consequently, a need has arisen to change the operational conditions in the subsequent step onward.

Further, in case of Comparative Example 2, where the concentration of acrylic acid in the bottom solution from the absorption column is maintained in like conditions as those in the Comparative Example 1, it is noted that the supply amount of the absorbent is required to be reduced, whereby the amount of the waste water is inevitably increased.

The method to capture (meth)acrylic acid according to the present invention can stably maintain the supply amount of the absorbent adapted to absorb the target product, the concentration of (meth)acrylic acid in the bottom solution from the absorption column, the absorbing coefficient and the amount of waste water drained during the whole process in the manufacturing process comprising introducing the gas containing (meth)acrylic acid into the absorption column and absorbing the target product as the solution by using the absorbent, whereby allowing to secure stable operation of the whole processes. In this respect, the absorbing method according to the present invention is highly useful from the industrial point of view.

The above-described operations and effects can be simply achieved by controlling the water amount contained in the gas exhausted from the top portion of the absorption column.

As described above, the absorbing method for (meth) acrylic acid according to the present invention is very useful since the method is characterized to be capable of allowing stable operation of the manufacturing process for (meth) acrylic acid by employing excellently simple means, and the absorbing apparatus as defined in the present invention is also useful for the industry since it can perform the foresaid absorbing method according to the present invention.

This application is based on Japanese patent application serial No. 2001-375741 filed on Dec. 10, 2001, whose priority is claimed under Paris convention, thus the contents thereof is incorporated by reference.

What is claimed is:

1. A method for absorbing (meth)acrylic acid, produced by a manufacturing process employing a catalytic gas-phase oxidation reaction, which method comprises introducing (meth)acrylic acid-containing gas, produced by the manufacturing process, into an absorption column, containing an absorbent comprising water as the main component, to absorb (meth)acrylic acid and form a solution of (meth) acrylic acid, discharging the solution of (meth)acrylic acid from a bottom portion of the absorbent column, and exhausting a water-containing gas from a top portion of the absorption column; wherein the concentration of (meth)acrylic acid in the solution discharged from the bottom portion of the absorbent column is controlled by changing the amount of water contained in the gas exhausted from the top portion of the absorption column.

2. The method according to claim 1, wherein the changing of the amount of water in the gas exhausted from the top portion of the absorption column is effected by controlling the temperature in the top portion of the absorption column.

3. The method according to claim 1, wherein the changing of the amount of water in the gas exhausted from the top portion of the absorption column is effected by controlling the pressure in the top portion of the absorption column.

4. The method according to claim 1, wherein the changing of the amount of water in the gas exhausted from the top portion of the absorption column is effected by controlling the temperature and the pressure in the top portion of the absorption column.

5. The method according to claim 1, which further comprises discharging waste water during the manufacturing process for producing (meth)acrylic acid, wherein a part or the whole of the waste water is recycled to the absorbent column to be used as the absorbent.

6. The method according to claim 2, which further comprises discharging waste water during the manufacturing process for producing (meth)acrylic acid, wherein a part or the whole of the waste water is recycled to the absorbent column to be used as the absorbent.

7. The method according to claim 3, which further comprises discharging waste water during the manufacturing process for producing (meth)acrylic acid, wherein a part or the whole of the waste water is recycled to the absorbent column to be used as the absorbent.

8. The method according to claim 4, which further comprises discharging waste water during the manufacturing process for producing (meth)acrylic acid, wherein a part or the whole of the waste water is recycled to the absorbent column to be used as the absorbent.

9. The method according to claim 1, wherein a water-containing gas is employed for the catalytic gas-phase oxidation reaction in a reactor, and the amount of water contained in the gas exhausted from the top portion of the absorption column is changed according to the amount of water contained in the gas to be introduced into the reactor for performing the catalytic gas-phase oxidation reaction.

10. The method according to claim 2, wherein a water-containing gas is employed for the catalytic gas-phase oxidation reaction in a reactor, and the amount of water contained in the gas exhausted from the top portion of the absorption column is changed according to the amount of water contained in the gas to be introduced into the reactor for performing the catalytic gas-phase oxidation reaction.

11. The method according to claim 3, wherein a water-containing gas is employed for the catalytic gas-phase oxidation reaction in a reactor, and the amount of water contained in the gas exhausted from the top portion of the absorption column is changed according to the amount of water contained in the gas to be introduced into the reactor for performing the catalytic gas-phase oxidation reaction.

12. The method according to claim 4, wherein a water-containing gas is employed for the catalytic gas-phase oxidation reaction in a reactor, and the amount of water contained in the gas exhausted from the top portion of the absorption column is changed according to the amount of water contained in the gas to be introduced into the reactor for performing the catalytic gas-phase oxidation reaction.

13. The method according to claim 5, wherein a water-containing gas is employed for the catalytic gas-phase oxidation reaction in a reactor, and the amount of water contained in the gas exhausted from the top portion of the absorption column is changed according to the amount of water contained in the gas to be introduced into the reactor for performing the catalytic gas-phase oxidation reaction.

14. The method according to claim 1, wherein air is employed for the catalytic gas-phase oxidation reaction in a reactor, and the amount of water contained in the gas exhausted from the top portion of the absorption column is changed according to the amount of water contained in the air to be introduced into the reactor for performing the catalytic gas-phase oxidation reaction.

* * * * *